United States Patent [19]

Adams et al.

[11] 4,130,018
[45] Dec. 19, 1978

[54] ULTRASONIC TRANSDUCER WITH REFERENCE REFLECTOR

[75] Inventors: George L. Adams, Bayshore; David Aker, Huntington Station; David Silvermetz, Wantagh, all of N.Y.

[73] Assignee: Envirotech Corporation, Menlo Park, Calif.

[21] Appl. No.: 829,036

[22] Filed: Aug. 30, 1977

[51] Int. Cl.$^2$ .............................................. G01F 23/28
[52] U.S. Cl. .................................... 73/290 V; 73/644; 310/327; 310/335; 310/336
[58] Field of Search ................. 73/290 V, 1 DV, 642, 73/609, 644; 310/327, 335, 336; 340/1 L, 8 FT

[56] References Cited

U.S. PATENT DOCUMENTS

| 2,430,013 | 11/1947 | Hansell | 128/24 A |
|---|---|---|---|
| 3,357,246 | 12/1967 | Stearn et al. | 73/290 V |
| 3,376,438 | 4/1968 | Colbert | 310/327 |
| 3,394,586 | 7/1968 | Cross | 73/644 |
| 3,663,842 | 5/1972 | Miller | 73/642 |
| 3,794,866 | 2/1974 | McElroy et al. | 340/8 FT |
| 3,834,233 | 9/1974 | Willis et al. | 73/290 V |
| 3,890,423 | 6/1975 | Zacharias | 73/644 |

OTHER PUBLICATIONS

Emerson and Cuming, Inc., Technical Bulletin 14-2-1, "Eccospheres® IG-101", Rev. 9/75.
Inventron Industries Inc., "Level Control", p. 14.
*Electronics*, "Plastic Disk Makes Transducer Excel in Calculating Distances by Ultrasound", pp. 76, 78, May 25, 1978.

*Primary Examiner*—Stephen A. Kreitman
*Attorney, Agent, or Firm*—William S. Bernheim

[57] ABSTRACT

An ultrasonic transducer for a system for determining liquid levels by echo ranging composed of a housing including a piezoelectric crystal mounted within the housing to transmit acoustic waves, an impedance matching medium mounted within the housing adjacent the crystal and including a window layer and a diaphragm layer to transmit acoustic waves between the crystal and a gaseous environment which window layer is composed of a material having hollow glass spheres dispersed therein, and a dampening backing mounted in said housing to abut the crystal which backing includes a plurality of solid lead spheres; a tube mounted to extend from the housing to form a beam of acoustic waves propagated from said crystal, the tube having an end which is telescoped into the housing and spaced a short distance from the diaphragm to form a gap for flow communication; and a reference reflector assembly mounted to extend from adjacent said housing, which assembly includes a U-shaped member having two legs extending in slideable contact with the sidewall of the tube and further including a member connecting the two legs.

11 Claims, 5 Drawing Figures

FIG. 1

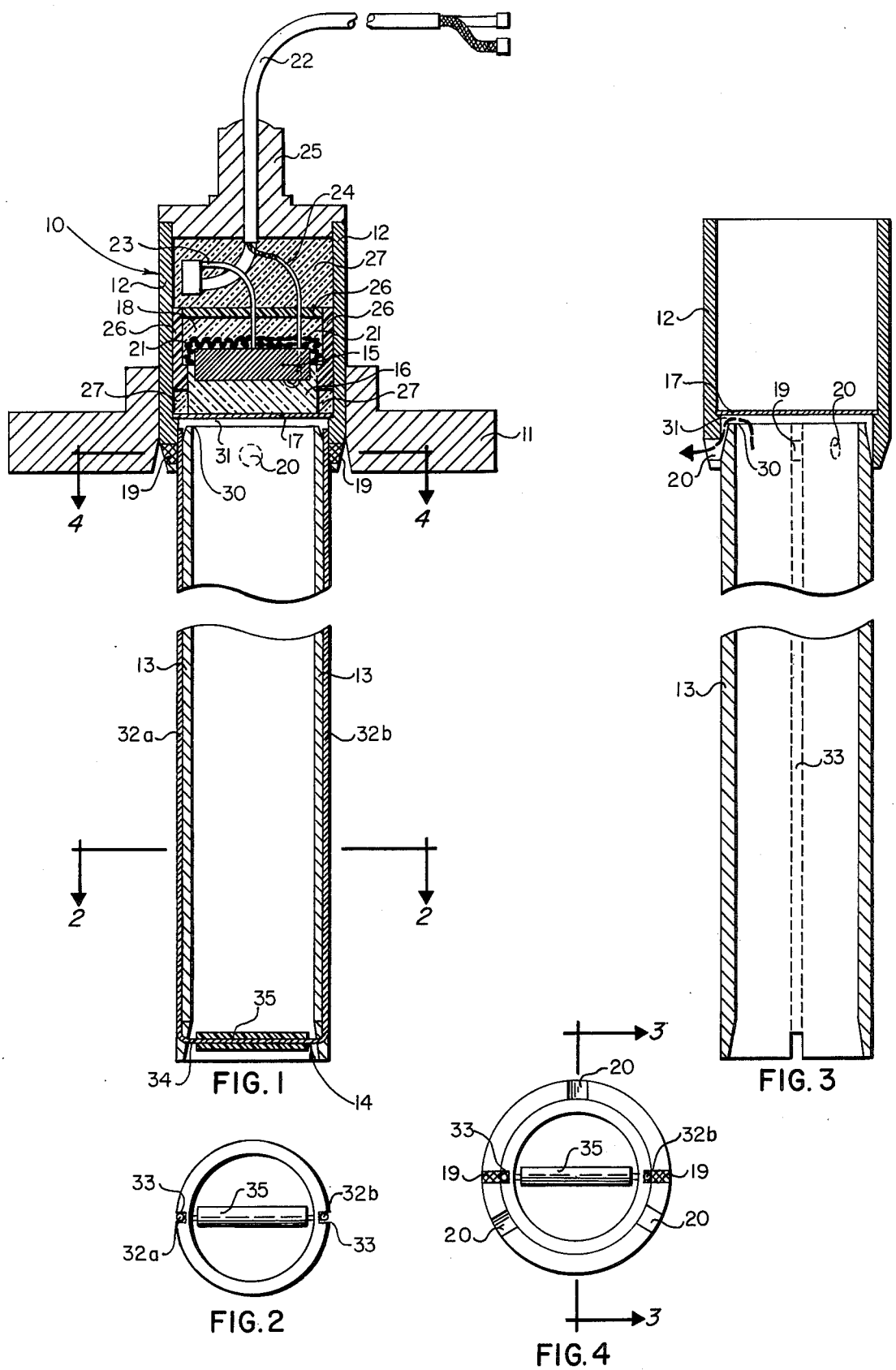

ULTRASONIC TRANSDUCER WITH REFERENCE REFLECTOR

BACKGROUND OF THE INVENTION

1. Field of the Invention

This invention relates to systems for sensing liquid levels and, more particularly, to systems utilizing ultrasonic transducers for determining liquid levels.

2. State of the Art

U.S. Pat. No. 3,834,233 to Willis et al. discloses a system for determining liquid level by echo ranging. The system includes a first ultrasonic transducer mounted at the top of a tank to direct acoustic wave energy down into the tank and detect an echo from the surface of the liquid contents of the tank. The distance from the first transducer to the surface is determined from a time measurement. Willis et al., in order to compensate for inaccuracies due to changes in the velocity of sound over the path the wave travels, position a second ultrasonic transducer at a fixed distance from the first transducer to detect the transmitted wave. Signals from the two detectors are processed to cancel the effects of any variation in the speed of sound.

Known transducers typically include a piezoelectric crystal sandwiched between a matching medium for improving energy transfer from the crystal to a gaseous environment and a backing for dampening ringing of the crystal (continued vibration of the crystal after excitation). The materials composing the medium and backing typically limit the temperature range at which the medium efficiently transfers acoustic energy and the backing efficiently dampens ringing.

U.S. Pat. No. 2,430,013 to Hansel discloses a matching medium positioned between a crystal and a water environment. Hansel teaches a medium thickness of an odd multiple of quarter wavelengths and the adusting of the acoustic impedance of a medium material by adding other finely divided materials including glass.

U.S. Pat. No. 3,995,179 to Flournoy discloses a backing composed of an epoxy resin having a plurality of pointed steel rods molded therein.

OBJECTS OF THE INVENTION

An object of this invention is to provide an ultrasonic transducer to accurately detect the level of a liquid surface in a vessel, independent of changes in the sound velocity characteristics of the gaseous environment in the vessel between the transducer and the liquid surface.

Another object is to provide an improved matching medium which matches the impedance of a piezoelectric crystal to a gaseous environment, which medium has relative constant acoustic impedance and sound velocity characteristics over a large range of temperatures.

Yet another object is to provide an improved dampening backing for a piezoelectric crystal capable of effectively eliminating excessive ringing of the crystal over a large range of temperatures.

BRIEF DESCRIPTION OF THE DRAWINGS

Further objects and advantages of the invention may be readily ascertained by reference to the following description and appended drawings, which are offered by way of description only and not in limitation of the invention, the scope of which is defined in the appended claims.

In the drawings

FIG. 1 is a cross section of an ultransonic transducer according to the present invention;

FIG. 2 is a cross section of the transducer of FIG. 1 taken along the line 2—2 for viewing in the direction of the arrows;

FIG. 3 is a cross section of the transducer of FIG. 1 taken along the line 3—3 in FIG. 4 for viewing in the direction of the arrows; in this view, various details of the transducer are omitted;

FIG. 4 is a cross section of the transducer of FIG. 1 taken along the line 4—4 for viewing in the direction of the arrows and FIG. 5 is an illustration of the circuitry in block form for an ultrasonic transducer according to the present invention.

DETAILED DESCRIPTION OF A PREFERRED EMBODIMENT OF THE INVENTION

Figure 5:
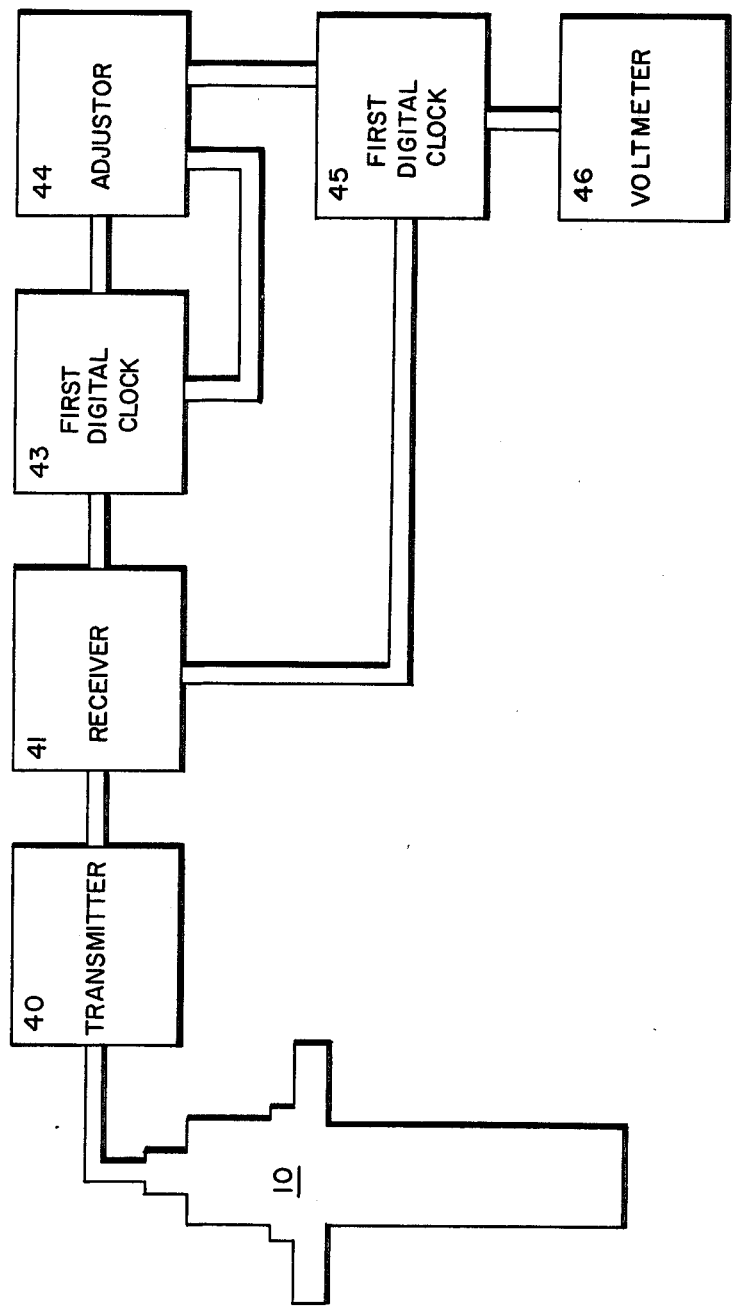

Referring to FIG. 1, an ultrasonic transducer 10 for use in a system for determining liquid level in a vessel, channel, etc. by the so-called echo ranging technique generally includes a housing 12 which contains a piezoelectric crystal to generate acoustic waves, an elongated tube fixed to the housing to form a beam of acoustic waves propagated from the crystal and a reference reflector assembly 14 which reflects a portion of the waves in the beam back to the crystal for calibration purposes. The housing 12 is composed of a material which prevents excessive ringing such as chlorinated polyvinyl chloride (CPVC). In practice, the transducer 10 can be mounted to a structure by means of a flange 11 attached to the housing.

Mounted within the housing 12 are acoustically active elements. The illustrated elements include a wafer-shaped piezoelectric crystal 15, acoustically transmissive layers 16 and 17 which match the acoustic output of the crystal 15 to the gaseous environment exterior to the transducer 10, and a wave dampening backing 18. The wafer-shaped crystal 15 is mounted so that the primary direction of wave propagation from the crystal 15, which is normal to the two faces of the crystal 15 is parallel to the longitudinal axis of the tube 13. A suitable material for the crystal 15 is lead zirconate titanate having a characteristic radial frequency of about 50 kilohertz. In practice the faces are coated, at least in part, with a conducting material such as silver. As used herein, the term "crystal" includes both the piezoelectric substance and the conducting coating.

The acoustically transmissive layers 16 and 17 form a matching medium which abuts the face of the crystal 15 towards the elongated tube 13. The nearer of the layers to the crystal 15 is a window layer 16 and the other is a diaphragm layer 17. To maximize energy transfer the medium has a thickness along the direction of wave propagation equivalent to an additive wave delay in the medium of about an odd multiple, preferably one, of one-quarter of the characteristic period of the crystal 15.

The window layer 16 of the medium is composed of a synthetic polymer material, preferably a polyurethane, having hollow glass spheres homogeneously dispersed therein to provide a substance having relatively constant acoustic impedance and sound velocity characteristics over a temperature range varying over about a hundred degrees celsius, for example from about −30° C. to 70° C. Preferably the glass spheres compose about 10% by weight of the window layer 16 and have diameters in the range of 20-300 microns. A preferred material for the glass spheres is sodium borosilicate. A preferred wall thickness for the spheres is about 2 microns. To provide the overall matching medium with relatively constant acoustic impedance and sound velocity characteristics, the window layer 16 accounts for about 90% of the total thickness of the medium or about nine times the thickness of the diaphragm layer 17.

The diaphragm layer 17 of the medium is laminated to the opposite side of the window layer 16 from the crystal 15. The primary purpose of the diaphragm layer 17 is to protect the inner parts of the housing 12 from the vessel environment. The diaphragm layer 17 is preferably composed of the same material as the housing 12.

The dampening backing 18 is positioned to abut the opposite face of the crystal 15 from the matching medium. Preferably, the backing 18 extends around the edges of the upper face of the crystal 15 to about one-half the thickness of the crystal 15 to also dampen propagation from the sidewall of the crystal 15. A preferred composition for the backing 18 includes a plurality of solid lead spheres 21 having diameters in the range of about 2 mm to 3 mm arranged in contact or close proximity with the crystal 15 and one another to absorb acoustic energy from the crystal 15. The interstices between the spheres are filled with a synthetic polymer material such as a polyurethane. In practice, this backing 18 prevents excessive ringing of the crystal 15 over a temperature range varying over about a hundred degrees Celsius, for example from about −30° C. to 70° C.

In the illustrated embodiment, the top of the housing 12 is sealed by a cap 25. Two wires 23 and 24 are threaded through the cap 25 to connect to the faces of the crystal 15. Additionally, the otherwise unfilled spaces in the housing 12 are filled with polyurethane foam 26 and solid polyurethane 27.

The housing 12 has a tubular sidewall which extends below the diaphragm 17 to provide means for mounting the tube 13. Through the sidewall are formed two slots 19 at diametrically opposed locations and three circular apertures 20 spaced at equal intervals around the sidewall.

The elongated tube 13 of the transducer 10 is mounted to extend vertically down from the housing 12. The tube 13 is composed of a material which prevents excessive ringing of the tube 13. Plastics, such as CPVC, are suitable. The upper tapered end 30 of the tube 13 is telescoped into the housing 12 and spaced a short distance below the diaphragm layer 17 to form a gap 31 about the top of the tube 13. The gap 31 provides a passage, in cooperation with the tapered end 30 and the three apertures 20 in the sidewall of the housing 12, for flow communication between the gas space enclosed at the end 30 of the tube 13 and the environment outside the tube 13.

The reference reflector assembly 14 of the transducer 10 includes a U-shaped rod attached to extend vertically downward from adjacent the housing 12 so that the tube 13 and the reflector assembly 14 can independently expand and contract with temperature. The rod includes two legs 32a and 32b connected at one end at the slots 19 to the housing 12 and tube 13. The legs 32a and 32b are in slideable contact with the exterior sidewall of tube 13 which is formed with two diametrically opposed grooves 33 into which the legs 32a and 32b fit for lateral support.

A bar 34, sheathed with a teflon tube 35 to provide a larger surface for reflecting acoustical waves, connects between the distal ends of the two legs 32a and 32b. The bar 34 extends normal to the direction of the wave propagation in the tube 13 at a typical distance of about 36 cm from the crystal. An additional minimum distance of about 9 cm between the bar 34 and a liquid surface is needed to detect the surface and distinguish it from the bar 34. The legs 32a and 32b are composed of a material having a low coefficient of thermal expansion so that the bar 34 remains at a relatively constant known distance from the crystal 15 over a temperature range varying over about a hundred degrees Celsius, for example from about −30° C. to 70° C. Most metals such as a stainless steel are suitable.

Electronic circuitry for operating the transducer 10 includes means 40 for transmitting acoustic waves from the crystal 15 as periodic pulses, means 41 for detecting the pulses as reflected by the bar 34, means 41 for detecting the pulses as reflected by a surface, first digital means 43 for counting initiated by the periodic pulse, means 44 for adjusting the speed of the count of the first digital means 43 so that the time interval during which the pulse travels from the crystal to the bar 34 and returns represents a constant count and a second digital means 45 for counting at a speed varying in proportion with the speed of the count of the first digital means 43 during the interval between the detection of the reflected pulse from the bar 34 and the detection of the reflected pulse from the surface.

For example, the electronic circuitry can include a common amplifier chain 41 for processing the reflected pulses from the bar 34 and the surface. The adjustment of the first digital means can be provided by a phase lock loop 44 in which the first digital means counts up to a constant. A single digital clock can provide the first and second digital means.

In practice, the ultrasonic transducer 10 is mounted on the top of a sealed tank holding a liquid. The tube 13 is positioned to extend vertically below the housing 12 in the gaseous environment of the sealed tank. The electronic circuitry periodically applies an electrical potential to excite the crystal to transmit a pulse of acoustic waves through the matching medium and down the tube 13 towards the surface of the liquid in the tank. The backing 18 dampens the acoustic waves transmitted from the top face of the crystal 15. Reflections of the pulse from the bar 34 and the liquid surface are detected by the crystal 15 before the crystal 15 is again excited by the circuitry.

As the pulse moves down the tube 13, a portion of the wave front strikes the bar 34 and is reflected back towards the crystal 15. This reflected pulse, upon striking, excites the crystal 15 to generate an electrical potential which is detected by the circuitry. When detected, the first digital means, which was previously initiated when the crystal 15 was initially excited, has or has not reached a predetermined constant. If the constant is reached by the first digital means 43 before the detection, the speed of the count is decreased and if the constant is reached after the detection, the speed of the count is increased. As adjusted the count is immediately initiated again from zero. The pulse continues downward past the bar 34, strikes the liquid surface and a portion of the wavefront is reflected back. Assuming the angle of the tube 13 is within several degrees of vertical a sufficient reflected pulse from the liquid surface reenters the tube 13 and excites the crystal 15 by striking it to generate an electrical potential which is detected by the circuitry. The count is again stopped and this second count is proportional to the unknown distance between the crystal 15 and the bar 34. The count can then be converted to a voltage and displayed on a voltmeter 46 to indicate a particular surface level. Regardless of changes in the speed of sound in the tank the same level produces the same second count. Changes in the velocity of sound are compensated for by the adjustments made in the speed of the first and second counts.

The flow communication through the gap 31 and apertures 20 prevents less dense components of the gas environment from becoming trapped in the tube 13 and producing sound velocity characteristics in the tube 13 which are not representative of the environment and as a consequence preventing the adjusting means 44 from accurately compensating for changes in the sound velocity characteristics of the environment.

The bar 34 of the reference reflector assembly 14 remains at a relatively constant distance from the crystal 15 regardless of temperature changes because of the low coefficient of thermal expansion characteristic of the legs 32a and 32b and their attachment adjacent the housing. The tube 13 is allowed to expand and contract with temperature changes according to its coefficient of thermal expansion which for plastics is typically higher than is acceptable for the legs 32a and 32b if high accuracy is to be achieved.

The transducer 10 can also be used to measure the distance to a solid object. When so used, vertical orientation of the tube 13 is not required.

We claim

1. An ultrasonic transducer for transmitting acoustic waves into a gaseous environment comprising:
   a. a piezoelectric crystal; and
   b. a window layer mounted adjacent said crystal to transmit acoustic waves between said crystal and a gaseous environment, said window layer composed of an acoustically transmissive material having dispersed therein hollow glass spheres having diameters in the range of 20–300 microns so that said window layer has a relatively constant acoustic impedance and sound velocity characteristic over a range of temperatures.

2. An ultrasonic transducer according to claim 1 wherein said spheres compose about 10% by weight of said window layer.

3. An ultrasonic transducer according to claim 1 further including a diaphragm layer mounted between said window layer and the gaseous environment; the total thickness of said window layer plus said diaphragm layer in the direction wave transmission being equivalent to a wave delay in said layers of about an odd multiple of one-quarter of the characteristic period of said crystal.

4. An ultrasonic transducer according to claim 3 wherein the thickness of said window layer is about nine times the thickness of said diaphragm layer.

5. An ultrasonic transducer according to claim 1 wherein the transmissive material is a polyurethane.

6. An ultrasonic transducer for a system for determining liquid levels by echo ranging comprising:
   a. a housing including a piezoelectric crystal mounted therein to transmit acoustic waves;
   b. a tube mounted to extend from said housing to form a beam of acoustic waves propagated from said piezoelectric crystal; and
   c. a reference reflector assembly mounted to extend from adjacent said housing, said assembly including a U-shaped member having two legs composed of material having a low coefficient of thermal expansion and positioned to extend in slideable contact with the sidewall of said tube along a substantial portion of their length and further including a member connecting the two legs and positioned normal to the direction of wave propagation in the tube so that said member reflects a portion of the transmitted waves back towards said crystal and the distance between said crystal and said member remains relatively constant over a range of temperatures.

7. An ultrasonic transducer according to claim 6 wherein the sidewall of said tube is formed with two diametrically opposed grooves in the sidewall of the tube into which said legs are positioned in slideable contact so that said legs receive lateral support.

8. An ultrasonic transducer according to claim 6 wherein said tube is composed of a plastic.

9. An ultrasonic transducer apparatus for a system for determining liquid levels by echo ranging comprising:
   a. a housing including a piezoelectric crystal mounted therein to transmit acoustic waves, a diaphragm layer mounted therein to separate said crystal from the gaseous environment outside said housing, said housing having a sidewall extending below said diaphragm layer and a plurality of apertures formed through said sidewall; and
   b. a tube mounted to extend from said housing to form a beam of acoustic waves propagated from said crystal, said tube having an end which is telescoped into said housing and spaced a short distance from said diaphragm layer to form a gap which provides, in cooperation with said plurality of apertures, a passage for flow communication between the gas space at the end of said tube and the environment outside said tube so that gases are not trapped in the gas space.

10. An ultrasonic transducer for transmitting acoustic waves into a gaseous environment for a system for determining liquid levels by echo ranging comprising:
   a. a housing including a piezoelectric crystal mounted therein to transmit acoustic waves, said housing having a sidewall;
   b. a window layer mounted within said housing adjacent said crystal to transmit acoustic waves between said crystal and a gaseous environment, said window layer composed of an acoustically transmissive material having dispersed therein hollow glass spheres having diameters in the range of 20–300 microns so that said window layer has a relatively constant acoustic impedance and sound velocity characteristic over a range of temperatures;
   c. a diaphragm layer to separate said crystal from the gaseous environment outside said housing;
   d. a dampening backing mounted within said housing to abut said crystal, said backing including a plurality of solid lead spheres in close proximity to said crystal and in contact with one another and further including a synthetic polymer material which fills the interstices between said plurality of spheres so that said backing prevents excessive ringing of the crystal over a range of temperatures;
   e. a plurality of aperatures formed through said sidewall;

f. a tube mounted to extend from said housing to form a beam of acoustic waves propagated from said crystal, said tube having an end which is telescoped into said housing and spaced a short distance from said diaphragm layer to form a gap which provides, in cooperation with said plurality of apertures, a passage for flow communication between the gas space at the end of said tube and the environment outside said tube so that gases are not trapped in gas space; and g. a reference reflector assembly mounted to extend from adjacent said housing, said assembly including a U-shaped member having two legs composed of material having a low coefficient of thermal expansion and positioned to extend in slideable contact with the sidewall of said tube along a substantial portion of their length and further including a member connecting the two legs and positioned normal to the direction of wave propagation in the tube so that said member reflects a portion of the transmitted wave back towards said crystal and the distance between said crystal and said member remains relatively constant over a range of temperatures.

11. A system for determining liquid levels by echo ranging comprising:

a. an ultrasonic transducer including i. a housing having a piezoelectric crystal mounted therein to transmit acoustic waves;

ii. a tube mounted to extend from said housing to form a beam of acoustic waves propagated from said piezoelectric crystal; and iii. a reference reflector assembly mounted to extend from adjacent said housing, said assembly including a U-shaped member having two legs positioned to extend in slideable contact with the sidewall of said tube along a substantial portion of their length and further including a member connecting the two legs and positioned normal to the direction of wave propagation in the tube so that said member reflects a portion of the transmitted waves back towards said crystal; and b. electronic circuitry connected to said transducer including i. means for transmitting acoustic waves from said crystal as periodic pulses in said tube;

ii. means for detecting the pulses as reflected by the said member;

iii. means for detecting the pulses as reflected by a surface back into said tube;

iv. first digital means for counting up to a constant and initiated by the periodic pulses;

v. means for adjusting the speed of the count of said first digital means so that the time interval during which the periodic pulse travels from said crystal to the said member and returns represents a constant count; and vi. a second digital means for counting at a speed varying in proportion with the speed of the count of the first digital means during the time interval between the detection of the reflected pulse from said member and the detection of the reflected pulse from the surface.

* * * * *